(12) United States Patent
Altvater et al.

(10) Patent No.: US 8,961,009 B2
(45) Date of Patent: Feb. 24, 2015

(54) X-RAY APPARATUS AND METHOD FOR CONTROLLING THE MOVEMENT OF AN X-RAY APPARATUS

(75) Inventors: Gregor Altvater, Hermosa Beach, CA (US); Stefan Sattler, Forchheim (DE); Stefan Schuster, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 246 days.

(21) Appl. No.: 13/415,063

(22) Filed: Mar. 8, 2012

(65) Prior Publication Data

US 2012/0236999 A1    Sep. 20, 2012

(30) Foreign Application Priority Data

Mar. 14, 2011    (DE) .......................... 10 2011 005 492

(51) Int. Cl.
*H05G 1/02* (2006.01)
*A61B 6/00* (2006.01)

(52) U.S. Cl.
CPC ............... *A61B 6/4441* (2013.01); *A61B 6/467* (2013.01); *A61B 6/547* (2013.01)
USPC ......................................................... 378/197

(58) Field of Classification Search
CPC ...... H05G 1/02; A61B 6/4441; A61B 6/4476; A61B 6/4482; A61B 6/035
USPC .......................................... 378/193, 196, 197
See application file for complete search history.

(56) References Cited

U.S. PATENT DOCUMENTS

| | | | |
|---|---|---|---|
| 4,475,071 A * | 10/1984 | Yoshizawa | 388/816 |
| 6,253,626 B1 * | 7/2001 | Shoberg et al. | 73/862.044 |
| 6,789,940 B2 | 9/2004 | Meyer et al. | |
| 7,160,027 B2 * | 1/2007 | Bauer et al. | 378/197 |
| 7,175,346 B2 * | 2/2007 | Heinze et al. | 378/197 |
| 2007/0200396 A1 | 8/2007 | Baumann et al. | |

FOREIGN PATENT DOCUMENTS

| | | |
|---|---|---|
| DE | 10140862 A1 | 4/2003 |
| DE | 102006008505 A1 | 8/2007 |
| DE | 102009004766 A1 | 7/2010 |
| DE | 102009008700 A1 | 8/2010 |

OTHER PUBLICATIONS

Translated version: Tietze et al.; "Electronic Circuits—Handook for Design and Application"; 2nd edition; pp. 1078-1079; 2002; Springer. Tietze, et. al.: Halbleiterschaltungstechnik, 13. issue, 2002, pp. 1056-1057.
Karl Hoffmann; "An Introduction to Measurements using Strain Gages", 1989; pp. 1-16, 36-49, 56-59; Publisher: Hottinger Baldwin Messtechnik GmbH, Darmstadt.

* cited by examiner

*Primary Examiner* — Jurie Yun (57) ABSTRACT

An X-ray apparatus is provided. The Xpray apparatus has a C-arm on which an X-ray source and an X-ray detector can be mounted opposite one another, at least one actuator for positioning the C-arm relative to a patient table, and a control device for controlling the actuator. The X-ray apparatus includes at least one sensor which detects a deformation of the C-arm at a first position of the C-arm and converts it into an output signal, the deformation of the C-arm being influenceable by a force exerted by an operator and applied directly or indirectly at a second position on the C-arm. The control device influences the actuator as a function of the output signal of the sensor. A method for controlling the movement of an X-ray apparatus is also described.

12 Claims, 6 Drawing Sheets

X-RAY APPARATUS AND METHOD FOR CONTROLLING THE MOVEMENT OF AN X-RAY APPARATUS

CROSS REFERENCE TO RELATED APPLICATIONS

This application claims priority of German application No. 10 2011 005 492.8 filed Mar. 14, 2011, which is incorporated by reference herein in its entirety.

FIELD OF INVENTION

The present invention relates to an X-ray apparatus having a C-arm on which an X-ray source and an X-ray detector can be mounted opposite one another, at least one actuator for positioning the C-arm relative to a patient table, and a control device for controlling the at least one actuator.

BACKGROUND OF INVENTION

Medical diagnostic and interventional systems in angiography, cardiology and neurology nowadays often use X-ray machines or X-ray devices as a basis for imaging. The X-ray machines are often equipped with a so-called C-arm. A C-arm mainly comprises an X-ray source and, disposed opposite it via a C-shaped, usually metal connecting structure, an X-ray detector. The C-arm can be stand- or ceiling-mounted. A plurality of movement axes, which can also be motorized, allow flexible positioning of the X-ray source and X-ray detector relative to an object under examination, e.g. a patient lying on the examination table. The positioning of the C-arm and of the components mounted thereon is also known as C-arm travel.

Figure 1:
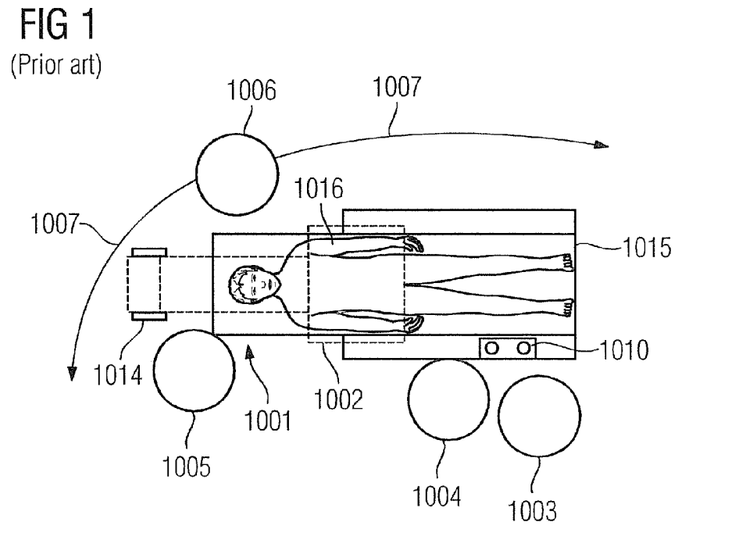
FIG. 1 schematically illustrates a treatment environment during medical diagnosis or intervention using an X-ray apparatus.

In the case of a diagnostic examination or a medical intervention, several people such as doctors, nurses or other medical technicians are often working in the examination room. By way of example, FIG. 1 shows a setup in which a patient 1016 an examination table 1015 is being examined using an X-ray apparatus 1001 comprising a C-arm 1002 which is in turn mounted on a stand 1014. A usual work sequence requires a structured division of responsibilities of the medical personnel involved and an expedient subdivision of the treatment room into different working areas of the respective personnel. For example, there tends to be a treating doctor 1004 at the side of the patient 1016, a nurse 1003 next to the treating doctor 1004, an anesthesiologist 1005 has his/her sphere of action at the head of the patient 1016, an assistant nurse 1006 has the largest radius of action and operates in the working area 1007. It is clear that during the examination the radii of action of the persons may change, possibly also overlap. In order to ensure a smooth treatment sequence, the position of the X-ray apparatus must be adapted to suit the changed conditions. In addition, different imaging positions require repositioning of the C-arm 1002. In the case of a freely positionable medical X-ray system, it can happen that very complex movements are necessary for re-positioning which require well trained personnel to execute same quickly and precisely using normal controls such as joysticks or pushbuttons 1010 disposed on the examination table. In addition, the situation may arise that simple movements such as changing the height of an X-ray detector could be carried out by personnel who, however, are far away from the controls 1010.

Hitherto, the position and attitude of the C-arm has been controlled by operator control modules mainly designed as joysticks and/or pushbuttons. The modules are mounted on the examination table or patient positioning table, on a trolley or in a separate room, the control room. In addition, there are fixed operator control switches with limited positioning capability which are mainly disposed on the X-ray detector. Additional C-arm system levers or handles with weight-compensated and smooth-acting mechanisms are used to extricate the patient in emergencies, e.g. in the event of system failure. In industrial applications, wireless operator control modules connected to the system via a radio link are known. The common feature of all these solutions is that an operator control is permanently mounted on the system at a particular location or must be carried by the user.

DE 10 2009 004 766 A1 discloses an X-ray device whose component parts are adjusted using a miniature model of the X-ray device, wherein manipulations of a model component part are translated into an adjustment of the corresponding component part. The disadvantage of this arrangement is that the miniature model is disposed at a central location and is usually operated only by one person.

SUMMARY OF INVENTION

The object of the invention is to propose an X-ray apparatus allowing decentralized and intuitive control of the movement of the X-ray apparatus. A method for controlling the movement of an X-ray apparatus shall also be specified.

This object is inventively achieved with an X-ray apparatus having the features set forth in the first independent claim and a method for controlling the movement of an X-ray apparatus having the features set forth in the second independent claim.

The basic concept of the invention is an X-ray apparatus having a C-arm on which an X-ray source and an X-ray detector can be mounted opposite one another, at least one actuator for positioning the C-arm relative to a patient table, and a control device for controlling the actuator. The X-ray apparatus comprises at least one sensor which detects a deformation of the C-arm at a first position of the C-arm and converts it into an output signal, said deformation of the C-arm being influenceable by a force exerted by an operator and directly or indirectly acting at a second position on the C-arm. The control device influences the actuator as a function of the sensor output signal.

The X-ray apparatus therefore comprises known components such as a C-arm, comprising an X-ray source and an X-ray detector, at least one actuator which, controlled by a control device, can move the C-arm to a desired position, said desired position relating to a patient positioning arrangement, e.g. in the form of an examination table on which a patient lies. The controlling of the actuator via the control device is now influenced such that an operator, e.g. a doctor, a nurse or a medical technician, applies a force at a point on the C-arm, i.e. the operator pushes against the C-arm at this location, causing the latter to bend or deform slightly not only at the point of application of the force. At usually another location on the C-arm, the deformation of the C-arm is measured using a sensor. The control device then controls the actuator taking into account the sensor output signal. The force can be exerted on the C-arm directly by the operator, i.e. the operator pushes against a point on the C-arm. However, the force can also be applied indirectly to the C-arm if, for example, the operator pushes against the X-ray detector, the X-ray source, or against another X-ray apparatus component fixedly connected to the C-arm.

The essential feature of the invention is that the positioning of the X-ray apparatus is no longer carried out centrally by an operator control device, but is initiated by measuring a deformation caused by pressure at one of a plurality of possible points on the C-arm.

A large part of the C-arm structure therefore becomes a kind of control, i.e. the limitation that the C-arm can only be controlled from one location, in some cases only by one person, no longer exists. By installing a small number of sensors, the implementation costs and complexity can be reduced compared to a solution achieving a comparable effect. Lastly, the operator control concept is intuitive, so that expensive training of the operating personnel, such as the training that would be required using e.g. pushbuttons or joysticks, is no longer necessary.

The control device can be an electronic computer. The actuator comprises, for example, electric motors, possibly with gears, hydraulic or pneumatic servo drives or a group of same. Actuators allow positioning of the C-arm, with translatory, rotatory or mixed translatory-rotatory motions being possible. The sensor(s) can be of the resistive, piezoelectric, optical, inductive or capacitive type.

The sensor is preferably implemented as a strain gage, in particular as a single-axis strain gage or multi-axis strain gage.

Strain gages are measuring devices for detecting tensile or compressive deformations. The most frequently used measuring effect is the change in the electrical resistance of a metallic material or of a semiconductor material when it deforms. Other types are capacitive, piezoelectric, photoelastic or mechanical strain gages. Metallic strain gages, which are often implemented as sensing grids made of resistance wire 3 to 8 µm thick on a thin plastic substrate, change their resistance even in the event of small deformations and are therefore best suited as strain sensors. Depending on the measurable direction of effect of stress states—single-axis, dual-axis, three-axis or spatial stress states—a distinction is drawn between single-axis and multi-axis strain gages. Other usable types are detailed e.g. in Karl Hoffmann, "An Introduction to Measurements using Strain Gages", published by Hottinger Baldwin Messtechnik GmbH, Darmstadt, 1989.

Another advantageous embodiment of the invention provides that the influencing of the actuator by the control device brings about a change in the position of the C-arm, the direction of the change including a component in the direction of the force exerted by the operator.

In other words, the C-arm is moved by the actuator, e.g. a motor, in a direction in which the operator attempts to push the C-arm. As the direction of motion of the actuator is usually predefined by an axis, or rather a translatory travel possibility, it may be sufficient if the direction of motion coincides with a force direction component. As a result, the operator will have the impression that his/her applied force would move the C-arm essentially in the direction of the force. This constitutes a very intuitive method for motor-assisted C-arm travel. At the same time, the method improves safety, as the change in position is aligned such that the C-arm evades the force and the movement comes to a halt if the operator ceases to apply force to the C-arm. Safety is further improved in that, in the event of a collision or if the C-arm comes up against an obstacle, the C-arm deforms counter to the direction of travel and therefore also counter to the direction of the force applied by the operator, thereby slowing down or stopping the movement of the C-arm.

In an advantageous further development, the rate of change in position of the C-arm is a function of the size of the deformation of the C-arm, the size of the deformation of the C-arm being detected by means of the sensor. In particular, a positive correlation exists between the rate of change in position of the C-arm and the detected size of the deformation of the C-arm.

This means that the travel speed depends on the C-arm deformation detected by the sensor and that when a large deformation is detected, the C-arm travels a higher speed than when a smaller deformation is detected. This can be based e.g. on a linear relationship or on a deformation/velocity pair assignment in the manner of a look-up table.

Depending on the geometric ratios of the C-arm and the placement of the sensor, different relationships can exist between the size of the deformation and the magnitude of the force exerted by the operator. For example, a linear relationship can exist, i.e. the deformation of the C-arm is proportional to the force exerted. However, the deformation can also depend on the point at which the force is applied, e.g. a lever action takes effect.

This feature makes the travel even more intuitive, as it provides an easily comprehensible relationship between size of force and travel velocity.

The sensor is advantageously placed on the C-arm or rather incorporated in the C-arm such that, in the event of deformation of the C-arm, the change in the output signal of the sensor is greater than for other possible placements on the C-arm or possible incorporations in the C-arm.

Depending on the geometric ratios of the C-arm, when a force is applied externally, the deformation will be of varying size at different points of the C-arm, i.e. the sensor will measure different deformation sizes depending on its position on the C-arm. In order to obtain a large sensor output signal, it is advisable to determine the C-arm position which exhibits a large or rather the maximum deformation in the event of a particular application of force. This position can be determined by a series of measurements in which the sensor signal is measured at a plurality of positions. Another possibility is to determine, by structural analysis of the C-arm, positions which exhibit a greater deformation than other positions when a directional force is applied. Such a structural analysis can be performed by mathematical calculation or by computer-assisted analysis, e.g. based on a finite element method (FEM). In the structural analysis, which can result in a mechanical structural model of the C-arm, geometric aspects and material properties of the C-arm must particularly take into account. Sensor placement relates to both the position of the sensor and its orientation, as both parameters affect the sensor signal for a given direction of action. The sensor can be mounted on the C-arm, e.g. by adhesive bonding or other attachment method or attachment means, or it can be incorporated in the material of the C-arm. A criterion for selecting the sensor position can be not only high sensor sensitivity to deformations but also selectivity in respect of the direction of action. For example, it is desirable that deformation of the C-arm in a direction in which the C-arm cannot travel also does not produce an output signal. This becomes increasingly important the more movement axes an X-ray machine possesses. It is also advisable to place a plurality of single-axis sensors or at least one multi-axis sensor such that the direction of an acting force can be reconstructed. For example, a plurality of single-axis strain gages can be positioned such that they are sensitive in differing degrees to applications of force from different directions, and the direction of force can therefore be reconstructed by linearly combining the individual sensor signals. In addition, general requirements such as good accessibility, simple attachment possibilities, etc. play a role in sensor positioning.

The deformation of the C-arm is detected at least essentially by two sensors, the difference between the sensor output signals being fed to the control device.

The use of two sensors whose output signals are subtracted from one another generally has the advantage, depending on the positioning of the sensors, that the difference signal is less prone to interference due to e.g. voltage, temperature, moisture, sensor material variations or aging effects or that the difference signal has a better level, i.e. signal-to-noise ratio. When a first sensor and a second sensor, termed a reference sensor, is used, the reference sensor can be placed such that a deformation of the C-arm does not significantly affect the output signal of the reference sensor. However, the output signal of the reference sensor changes in the same way as that of the first sensor in the event of a change in the operating conditions, such as temperature or humidity or operating voltage. By taking the difference, the sensor signals caused by variations in the operating conditions are compensated, so that only the sensor signal change due to the deformation of the C-arm undergoes further processing. Another possibility is to place the sensors such that the deformation of the C-arm in the case of the reference sensor changes inversely to that in the case of the first sensor, e.g. a placement of the sensors such that the deformation of the C-arm causes the first sensor to lengthen and the reference sensor to shorten. The difference between the two sensor signals is again compensated for operating condition fluctuations and has an amplitude twice as large as that of an individual sensor.

In another advantageous embodiment, the sensors of the X-ray apparatus are disposed in opposite branches of a bridge circuit and the output voltage of the bridge circuit is fed to the control device.

A bridge circuit, H-circuit, H-bridge or specifically a Wheatstone bridge is a device for measuring small changes in resistance. Particularly when using sensors, it is employed as a measuring transducer. It is known from the prior art and described, for example, in U. Tietze and Ch. Schenk, "Halbleiter-Schaltungstechnik" (Electronic Circuits), 13th edition, Springer-Verlag, Berlin, Heidelberg, 2010, p. 1056 et seq. The bridge circuit is generally comprised of three resistors, also known as bridge resistors, at least one bridge resistor being represented by the resistive sensor. The resistors are connected to form a closed ring or rather a quadrilateral, wherein the voltage source is in one diagonal and the voltage difference, known as the diagonal voltage, bridge transverse voltage or bridge voltage, is measured in the other diagonal. With bridge circuits, a distinction is drawn between quarter bridges in which one bridge resistor is variable, half bridges in which two bridge resistors are variable, and full bridges in which four bridge resistors are variable. The non-variable bridge resistors are usually calibrated precision resistors having resistance values of the order of magnitude of the sensor resistors. When at least two sensor resistors are used, they are preferably arranged such that, in the event of C-arm deformation, the resistances change inversely, and similar effects, caused e.g. by temperature, voltage or humidity fluctuations, compensate one another.

Another advantageous embodiment of the invention provides that the control device for controlling the actuator takes into account the output signal of the sensor and an expected value for the output signal of the sensor, wherein the expected value for the output signal of the sensor can be calculated by means of a structural model of the C-arm and/or of the X-ray source and/or of the X-ray detector.

As a result of the mechanical flexibility of modern C-arm systems, small deformations or deflections of the C-arm occur even during normal travel processes, i.e. processes without e.g. additional force being applied by an operator or obstacles. As these deformations are also detected by the sensors, the control device of the X-ray apparatus cannot initially discriminate between these inherent deformations and a deformation caused by an externally applied force. With the aid of a structural model incorporating the geometrical aspects and material properties of the C-arm and associated components of the X-ray apparatus, an expected value for the output signal of the sensor without externally applied force can be calculated. The absolute value and the direction of the externally applied force can be inferred from the comparison, e.g. the difference between the expected value for the output signal of the sensor and the measured sensor output value. The structural model can comprise an analytical mathematical model whose parameters are provided by specifications, e.g. from material tables, or derived from measurements. The structural model parameters can represent physical features of the C-arm system, such as e.g. the weight of the X-ray detector or the module of elasticity of the C-arm. Also conceivable, however, are structural models whose parameters, so-called fitting parameters, are not directly assignable to physical features, and whose values are adjusted by series of measurements and optimization methods. For rotatory movement possibilities there often exists, to a first approximation, a sinusoidal relationship between angle of rotation and deformation. Other movements may also have linear, square-law and other relationships.

The calculation of the expected value for the output signal of the sensor advantageously takes into account a model of the mechanical structure of the C-arm and/or of the X-ray source and/or of the X-ray detector, and/or the material properties of the components of the C-arm and/or of the X-ray source and/or of the X-ray detector, and/or the position of the C-arm and/or of the X-ray source and/or of the X-ray detector, and/or the movement of the C-arm and/or of the X-ray source and/or of the X-ray detector, and/or the acceleration of the C-arm and/or of the X-ray source and/or of the X-ray detector.

The mechanical structure of the C-arm, the material properties of the components of the C-arm, the position and orientation of the C-arm, the movement of the C-arm and the acceleration of the C-arm affect the deformation of the C-arm, also independently of an external force. For example, if the C-arm is accelerated during a movement, the C-arm will bend because of the inertia of the accelerated mass. For an unambiguous interpretation of the sensor signal, this deformation is taken into account. In addition to the modeling of the C-arm, preferably components connected to the C-arm, e.g. the X-ray detector, the X-ray source, handles and other attachments, are also incorporated in the model, as these generally also contribute to the statics and dynamics of the X-ray system. It is generally the case that the quality of the expected value increases the more accurately the system and the dynamics of the X-ray apparatus are modeled. A structural model of the X-ray apparatus taking the dynamics into account can also be termed a dynamic model of the X-ray apparatus. In contrast to a force exerted by an operator, gravity, accelerational and inertial forces can be termed regular system forces.

Another basic concept of the invention relates to a method for controlling the movement of an X-ray apparatus having a C-arm on which an X-ray source and an X-ray detector can be mounted opposite one another, at least one actuator for positioning the C-arm relative to a patient table, and a control device for controlling the at least one actuator. At least one sensor detects a deformation of the C-arm at a first position of the C-arm and translates the deformation into an output signal, said deformation of the C-arm being influenceable by a force applied by an operator and directly or indirectly exerted at a second position on the C-arm. The control device influences the actuator as a function of the output signal of the sensor.

Particularly advantageously, the method for controlling the movement of an X-ray apparatus comprises the following steps:
a) Detecting the measured value for the deformation of the C-arm at the first position of the C-arm using a measuring element comprising the at least one sensor, in particular at least one strain gage, wherein the deformation of the C-arm is influenceable by the force applied by the operator and exerted directly or indirectly at second position on the C-arm;
b) Calculating an expected value for the measured value of the deformation of the C-arm at the first position of the said expected value being determined using a structural model or a dynamic model which takes into account the mechanical structure of the C-arm and/or of the X-ray source and/or of the X-ray detector, and/or the material properties of the components of the and/or of the X-ray source and/or of the X-ray detector, and/or the current position of the C-arm and/or of the X-ray source and/or of the X-ray detector, and/or the current movement of the and/or of the X-ray source and/or of the X-ray detector, and/or the current acceleration of the C-arm and/or of the X-ray source and/or of the X-ray detector;
c) Taking the difference between the measured value for the deformation of the C-arm at the first position of the C-arm and the expected value for the measured value of the deformation of the at the first position of the C-arm;
d) Calculating a control signal using a controller which is in particular a component part of the control device, such that an absolute-value increase in the difference is counteracted;
e) Supplying the control signal for a final control element which is in particular a component part of the actuator;
f) Repeating steps a) to e) until an abort criterion is fulfilled, in particular by actuation of the switch.

The examples described in greater detail below represent preferred embodiments of the present invention.

BRIEF DESCRIPTION OF THE DRAWINGS

Other advantageous further developments will emerge from the following description and accompanying drawings in which.

DETAILED DESCRIPTION OF INVENTION

Figure 2:
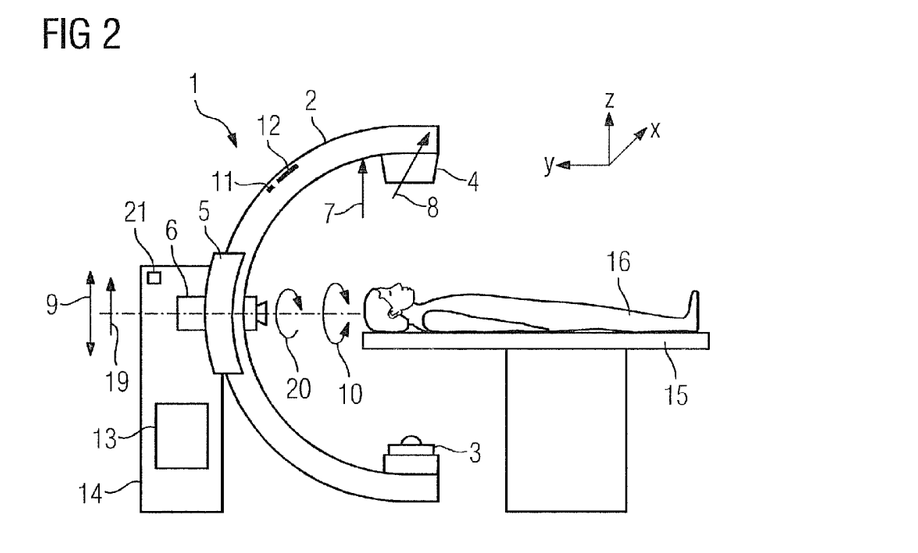
FIG. 2 shows an exemplary embodiment of the X-ray apparatus according to the invention.

FIG. 2 shows an exemplary embodiment of the X-ray apparatus 1 according to the invention. It comprises a C-arm 2 on which an X-ray source 3 and an X-ray detector 4 are mounted opposite one another. The C-arm 2 is connected to a stand 14. The C-arm 2 can be moved in the z-direction, i.e. in the vertical direction 9, by a first actuator 5, e.g. an electric motor. The C-arm 2 can be rotated about an axis parallel to the y-axis, i.e. about a horizontal axis 10, by a second actuator 6, e.g. an electric motor with gearbox. The movement of the C-arm 2 changes the position of the X-ray source 3 and of the X-ray detector 4 relative to a patient table 15, here an examination table, on which an object under examination 16, here a patient, is lying. Mounted on the C-arm 2 are a first sensor 11 and a second sensor 12 which are implemented as strain gages. If an operator, e.g. a doctor, applies a first force 7 in the z-direction to the upper region of the C-arm 2, i.e. pushes against the C-arm in the z-direction, the upper part of the C-arm 2 will deform slightly in the z-direction. The deformation produces a compressive effect at the position of the first sensor 11. The compression is detected by the first sensor 11 and converted into an e.g. electrical output signal. The output signal is forwarded to a control device 13, e.g. an electronic computer, which influences the first actuator 5 such that the C-arm 2 is moved in the direction 19, i.e. in the direction of the z-axis. If the operator applies a second force 8 to the upper region of the C-arm 2 in the x-direction, i.e. pushes against the C-arm in the x-direction, the upper part of the C-arm 2 will bend slightly in the x-direction. The bending produces an extension effect at the position of the second sensor 12. The extension is detected by the second sensor 12 and converted into an output signal. The output signal is forwarded to the control device 13 which influences the second actuator 6 such that the C-arm 2 executes a rotational movement 20, i.e. a movement about an axis parallel to the y-axis. An operator control unit 21, which is implemented e.g. as a switch, enables the movement to be halted. This illustrates the intuitive motion control of the X-ray apparatus 2, which requires no specialized knowledge: lateral pressure 8 on the C-arm 2 causes the C-arm 2 to rotate in the direction 20 of the pressure until the desired position is reached and the operator ends the pressure 8. The position of the point of pressure is not limited to the position indicated by the reference character 8, but can vary across a range.

Figure 3:
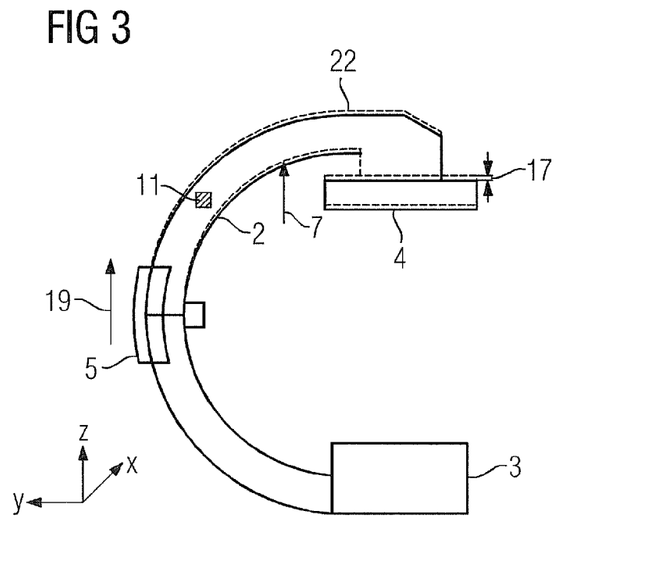
FIG. 3 shows a side view of another exemplary embodiment of part of the X-ray apparatus according to the invention.

FIG. 3 shows a side view of another example of part of the X-ray apparatus. The C-arm 2 again comprises the X-ray source 3, the X-ray detector 4, the actuator 5 and the sensor 11. Pressure 7 on the C-arm 2 in the upper region of the C-arm in the z-direction causes the upper part of the C-arm to bend and assume the shape 22, the X-ray detector 4 being displaced by the distance 17. The bending of the C-arm is detected by the sensor 11. A control device (not shown) connected to the sensor 11 receives the sensor signal and controls the actuator 5 such that the C-arm 2 is caused to travel in the direction 19, i.e. in the z-direction.

Figure 4:
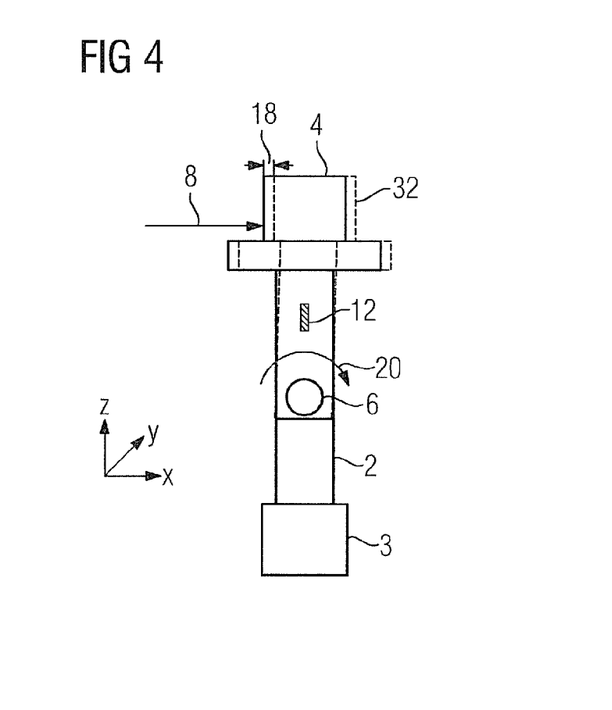
FIG. 4 shows a front view of the other exemplary embodiment of the part of the X-ray apparatus according to the invention.

FIG. 4 shows a front view of the other example of part of the X-ray apparatus. The C-arm 2 again comprises the X-ray source 3 and the X-ray detector 4. The actuator 6 can rotate the C-arm about the y-axis, the sensor 12 is placed and oriented on the C-arm 2 such that it can detect bending of the C-arm 2 in the direction of the x-axis. Pressure 8 on the C-arm 2 in the upper region of the C-arm in the x-direction causes the upper part of the C-arm to bend, the X-ray detector 4 being displaced by the distance 18 and assuming the position 32. The bending of the C-arm is detected by the sensor 12. The control device (not marked) is connected to the sensor 12, receives the sensor signal and controls the actuator 6 such that the C-arm 2 is rotated in the direction 20.

Figure 5:
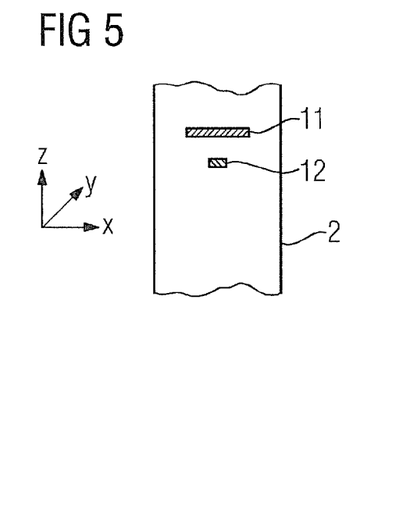
FIG. 5 shows an example of placement of the strain gage in a front view of a C-arm.

By way of example, FIG. 5 is a front view of a section of the C-arm 12 showing the position and orientation of two sensors implemented as a single-axis strain gage. The Cartesian coordinate system from FIG. 3 and FIG. 4 applies. A force acting in the x-direction and deforming the C-arm 2 in the x-direction is detected almost exclusively by the first strain gage 11, i.e. bending of the C-arm 2 in the x-direction produces a resistance change in the first strain gage 11, whereas the resistance value of the second strain gage 12 does not change significantly.

Figure 6:
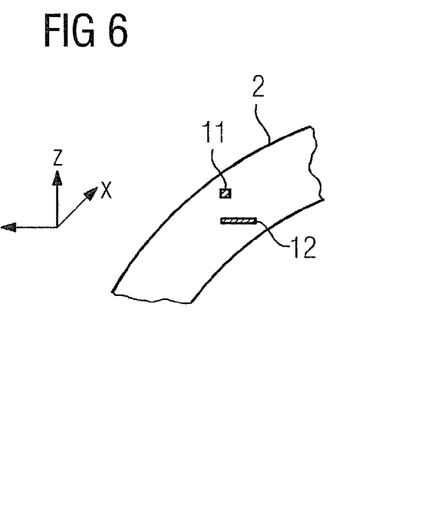
FIG. 6 shows an example of placement of the strain gage in a side view of a C-arm.

FIG. 6 shows a side view of the section of the C-arm 2 known from FIG. 5 with the two sensors which are implemented as a single-axis strain gage. The Cartesian coordinate system from FIG. 3 and FIG. 4 again applies. A force acting in the z-direction and deforming the C-arm 2 in the z-direction is detected almost exclusively by the second strain gage 12, i.e. bending of the C-arm 2 in the z-direction produces a resistance change in the second strain gage 12, whereas the resistance value of the first strain gage 11 does not change significantly.

Figure 7:
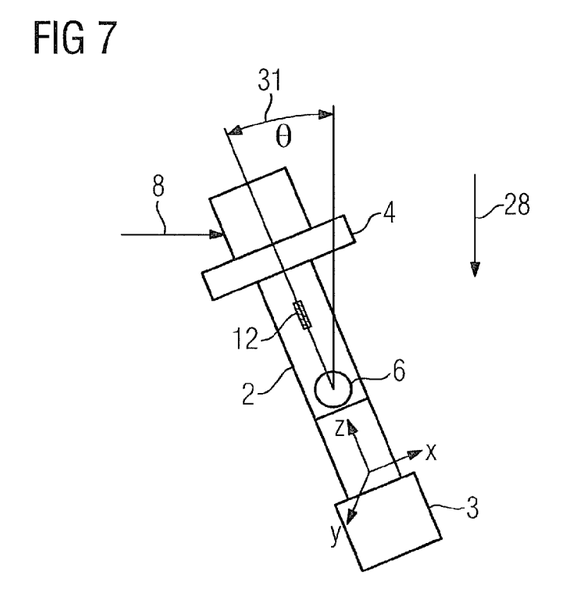
FIG. 7 shows an exemplary embodiment of a C-arm having a rotational movement about the y-axis.

FIG. 7 shows another example of a C-arm 2 with X-ray source 3, X-ray detector 4, actuator 6 and sensor 12. The C-arm 2 is rotated through a deflection angle θ 31 from the neutral θ=0° position. A Cartesian coordinate system with x-, y- and z-axis is associated with the C-arm 2. In addition to gravity 28, an external force 8 is applied to the X-ray detector 4. The sensor 12 is implemented as a resistive strain gage system which can detect deformations of the C-arm 2 in the x-direction and in the z-direction. To measure deformation in the z-direction, a two-part strain gage sensor is used whose sensing surface is placed such that, in the event of deformation of the C-arm in the z-direction, the first part is extended whereas the second part is compressed, or the first part is compressed whereas the second part is extended.

Figure 8:
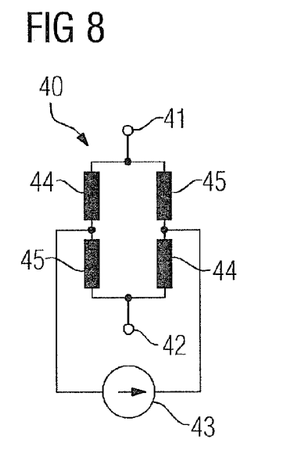
FIG. 8 shows an exemplary embodiment of a bridge circuit for measuring deformation in the x-direction.

A possible electronic circuit 40 for evaluating the x-direction-sensitive sensor 12 is shown in FIG. 8. The circuit 40 is a half bridge circuit operated at e.g. 3 to 15 VDC, characterized by an upper operating voltage 41 and a lower operating voltage 42. The two measuring resistors 44 disposed diagonally in the bridge circuit represent the resistors of the x-direction-sensitive sensor 12, their resistance values varying as a function of any deformation of the C-arm 2 from FIG. 7 in the x-direction. The resistors 45 of the electronic circuit 40 are implemented as calibrated precision resistors whose resistance values are in the order of the nominal resistance values of the measuring resistors 44, e.g. 120Ω). The series-connected resistors 44 and 45 in each case form voltage dividers whose voltages at the midpoint nodes vary with the resistance value of the measuring resistors 44. Due to the arrangement of the resistors 44 and 45, the two midpoint node voltages behave in an inverse manner. The size of the deformation and the type of deformation, i.e. extension or compression, of the strain gage and hence the deformation of the C-arm 2 can be inferred from the voltage 43 which is measured between the potentials of the midpoint nodes and is termed the bridge output voltage.

Figure 9:
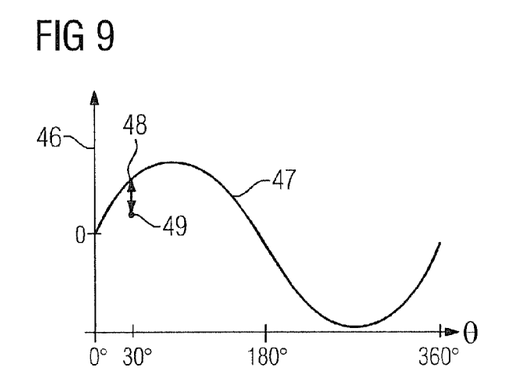
FIG. 9 shows a typical voltage waveform of a bridge circuit for measuring the deformation in the x-direction and a measured value.

FIG. 9 shows a typical graphical analysis of the electrical properties of the circuit 40 from FIG. 8. The graph shows the bridge output voltage 43 in volts (vertical axis 46) versus the deflection angle θ 31 in degrees. The continuous line 47 corresponds to the bridge output voltage 42 of the x-direction-sensitive sensor 12 when no external force 8 is applied. The sinusoidal shape of the bridge output voltage 42 is explained by the proportion of gravity 28 from FIG. 7 acting in the x-direction. For a deflection angle θ=0° or θ=180°, the C-arm 2 is not deformed in the x-direction. The two measuring resistors 44 therefore have the same resistance value as the other resistors 45 and the bridge output voltage 43 is zero. For other deflections, the C-arm 2 deforms slightly due to gravity 28, causing the bridge output voltage 43 to assume non-zero values. Depending on the direction of the deformation, the bridge output voltage 43 is greater or less than zero. For a deflection angle θ=30°, in the absence of an externally applied force a bridge output voltage 48 greater than zero is produced. If the external force 8 is applied to the C-arm 2, a bridge output voltage 49 is produced which is less than the bridge output voltage 48. This can be explained qualitatively in that, due to gravity 28, the C-arm 2 is subjected to a deformation component in the negative x-direction which is partly compensated again by the effect of the force 8, as the force 8 has a component which deforms the C-arm 2 in the direction of the positive x-axis. If the deflection angle θ and the response of the bridge output voltage 47 over the deflection angle θ without externally applied force are known, the external force 8 can be inferred by comparison with the measured bridge output voltage 49. The output voltage 47 as a function of the deflection angle θ can be interpreted as a target curve which is compared with the measured actual values 49. Any deviation of the actual value 49 from the target value 48 is fed to a control device, e.g. an electronic computer, which then controls the actuator 6 from FIG. 7 using a control algorithm, for example.

Figure 10:
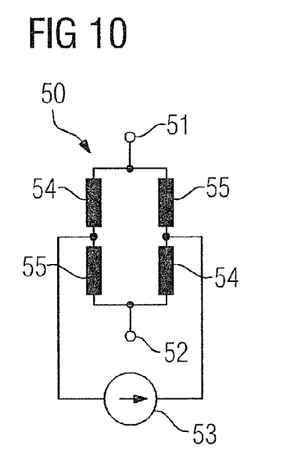
FIG. 10 shows an exemplary embodiment of a bridge circuit for measuring deformation in the z-direction.

FIG. 10 shows an embodiment of a circuit 50 for evaluating the z-direction-sensitive sensor 12 from FIG. 7. The circuit 50 is implemented as a full-bridge circuit operated with a DC voltage, characterized by an upper operating voltage 51 and a lower operating voltage 52. The two first measuring resistors 54 disposed diagonally in the bridge circuit represent the resistors of the first section of the z-direction-sensitive sensor 12, whose resistance values change as a function of a z-direction deformation of the C-arm 2 from FIG. 7. The second measuring resistors 55 of the electronic circuit 50 represent the resistors of the second section of the z-direction-sensitive sensor 12, whose resistance values likewise change as a function of a z-direction deformation of the C-arm 2. However, the way the sensor 2 is positioned causes the resistance values of the measuring resistors 54 and 55 to change in an inverse manner, since a deformation of the C-arm 2 in the z-direction produces an extending or compressing effect in the first section of the sensor 12, with the opposite effects occurring in the second section of the sensor 12. The series connected measuring resistors 54 and 55 each constitute voltage dividers whose voltages at the midpoint nodes vary with the resistance values of the measuring resistors 54 and 55. In addition, due to the arrangement of the resistors 54 and 55, the two midpoint node voltages also behave in an inverse manner in the event of deformation of the C-arm. The size of the deformation and type of deformation, i.e. extension or compression in relation to the z-axis, of the strain gage and therefore the deformation of the C-arm 2 can be inferred from the voltage 53 measured between the midpoint node potentials and referred to as the bridge output voltage.

Figure 11:
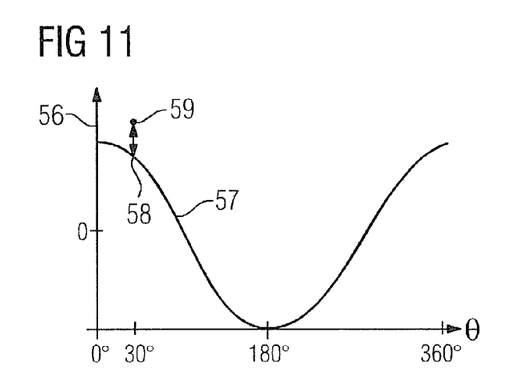
FIG. 11 shows a typical voltage waveform of a bridge circuit for measuring the deformation in the z-direction and a measured value.

In FIG. 11 shows a typical graphical analysis of the electrical properties of the circuit 50 from FIG. 10. The graph shows the bridge output voltage 53 in volts (vertical axis 56) versus the deflection angle θ 31 in degrees. The continuous line 57 corresponds to the bridge output voltage 42 of the z-direction-sensitive sensor 12 when no external force 8 is applied. The sinusoidal shape of the bridge output voltage 52 is explained in that, for a deflection angle θ=0° or θ=180°, the C-arm 2 is deformed maximally in the z-direction, so that the two measuring resistors 54 and 55 have maximally different resistance values and the bridge output voltage 53 therefore assumes maximum values. For other deflections, the C-arm 2 deforms less due to gravity 28, causing the bridge output voltage 53 to assume values between the maxima. For a deflection angle θ=90° or θ=270°, the bridge output voltage 53 is ideally zero. For a deflection angle θ=30°, in the absence of an externally applied force a bridge output voltage 58 is produced. If the external force 8 is applied to the C-arm 2, a bridge output voltage 59 is produced which is greater than the bridge output voltage 58. This can be explained qualitatively in that, due to gravity 28, the C-arm 2 is subjected to a deformation component in the negative z-direction which is amplified still further by the effect of the force 8, as the force 8 has a component which likewise deforms the C-arm 2 in the direction of the negative z-axis. If the deflection angle θ and the response of the bridge output voltage 57 over the deflection angle θ without externally applied force are known, the external force 8 can be inferred by comparison with the measured bridge output voltage 59. The output voltage 57 as a function of the deflection angle θ can again be interpreted as a target curve which is compared with the measured actual values 59. Any deviation of the actual value 59 from the target value 58 is fed to a control device, e.g. an electronic computer which then controls the actuator 6 from FIG. 7 using a control algorithm, for example.

Figure 12:
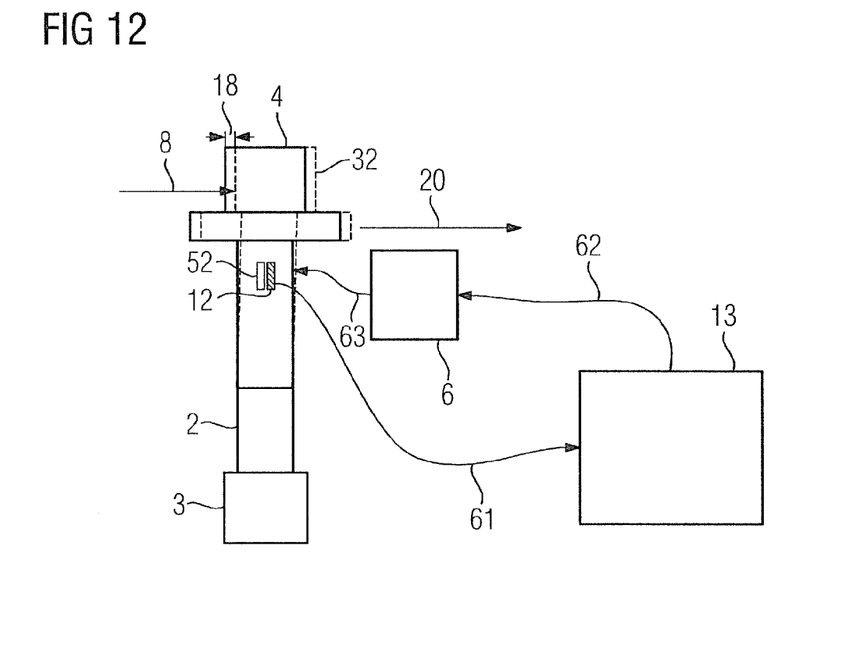
FIG. 12 shows an example of the execution of a force-assisted movement.

FIG. 12 schematically illustrates an exemplary embodiment for the sequence of force-assisted travel of a C-arm 2. The C-arm 2 comprises an X-ray source 3 and an X-ray detector 4. An external force 8 is applied by an operator (not shown) to an X-ray detector 4 which is thereby caused to move to a second position 32 while at the same time slightly distorting the C-arm 2. A sensor system implemented as a strain gage 12 and a reference strain gage 52 detects the deformation of the C-arm 2 and, in a step 61, transmits the signal representing the difference between the output signal of the strain gage 12 and the output signal of the reference strain gage 52 to the control device 13. The control device 13 comprising, for example, an electronic computer calculates an expected value for the measured value of the deformation of the C-arm 2 at the position of the sensor system with the aid of a structural model or a dynamic model which takes into account the mechanical structure of the C-arm 2, the material properties of the components of the C-arm 2, the current position of the C-arm 2, the current movement of the C-arm 2 and the current acceleration of the C-arm 2. From the comparison of the expected value for the measured value of the deformation of the C-arm 2 with the actual measured value of the deformation, e.g. by taking the difference, the direction and the absolute value of the external force acting on the C-arm 2 at the position of the sensor or at another position on the C-arm 2 is calculated. From the information concerning the direction and absolute value of the external force, the control device 13 calculates the control signal for an actuator 6 such that an absolute value increase in the difference is counteracted, i.e. the structural model or the dynamic model also includes actuator modeling which goes into a control algorithm. The preferably electronic control signal is communicated to the actuator 6 in a step 62. In a step 63, the actuator 6, which is implemented e.g. as a motor, translates the electronic control signal into a mechanical movement or rather a mechanical torque, causing the C-arm to travel in a direction 20 which comprises at least one directional component of the external force. The entire sequence is preferably repeated continuously or rather in rapid succession, e.g. fifty times per second, so that the travel process follows the movement requirements of the operator without noticeable delay. The process ends when, for example, an off-switch is actuated.

Figure 13:
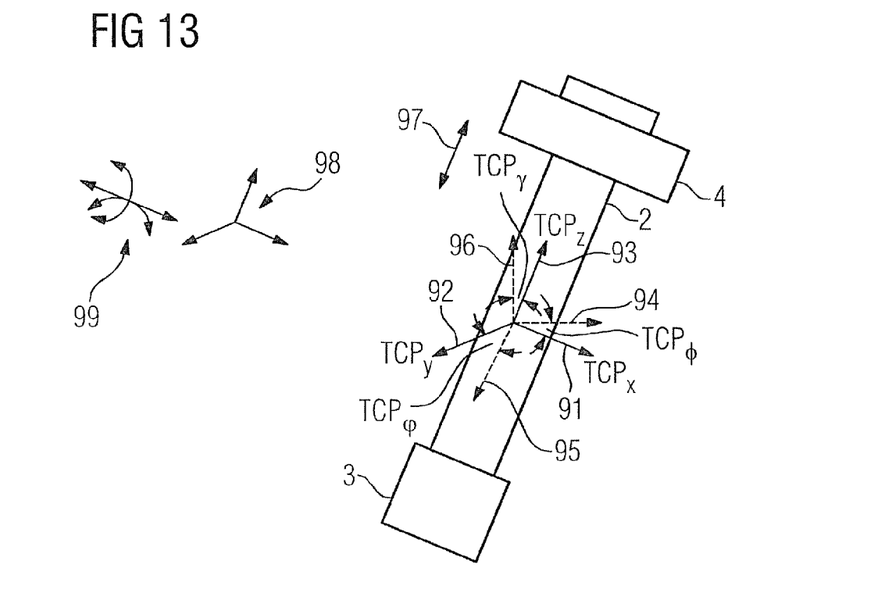
FIG. 13 shows an example of coordinate systems and motion vectors of the C-arm.

FIG. 13 shows by way of example possible coordinate systems and motion vectors of a C-arm 2 comprising an X-ray source 3 and an X-ray detector 4. To describe the position of the C-arm 2 in space, a local coordinate system is preferably used which is attached to a central point of the C-arm 2, the so-called tool center point, TCP, and moves with the C-arm 2, relative to a fixed measuring system. The local coordinate system attached to the C-arm 2 comprises the coordinate axes $TCP_x$ 91, $TCP_y$ 92 and $TCP_z$ 93, the reference system comprising the coordinate axes $TCP_\phi$ 94, $TCP_\phi$ 95 and $TCP_y$ 96. The C-arm 2 can execute translatory movements in the direction of the axes of the coordinate system 98 or more specifically linear combinations thereof or also translatory movements in the directions of the movement arrows 99. The C-arm 2 also has a movement component 97 whereby the so-called source-image distance, i.e. the distance between X-ray source 3 and X-ray detector 4, can be varied.

Figure 14:
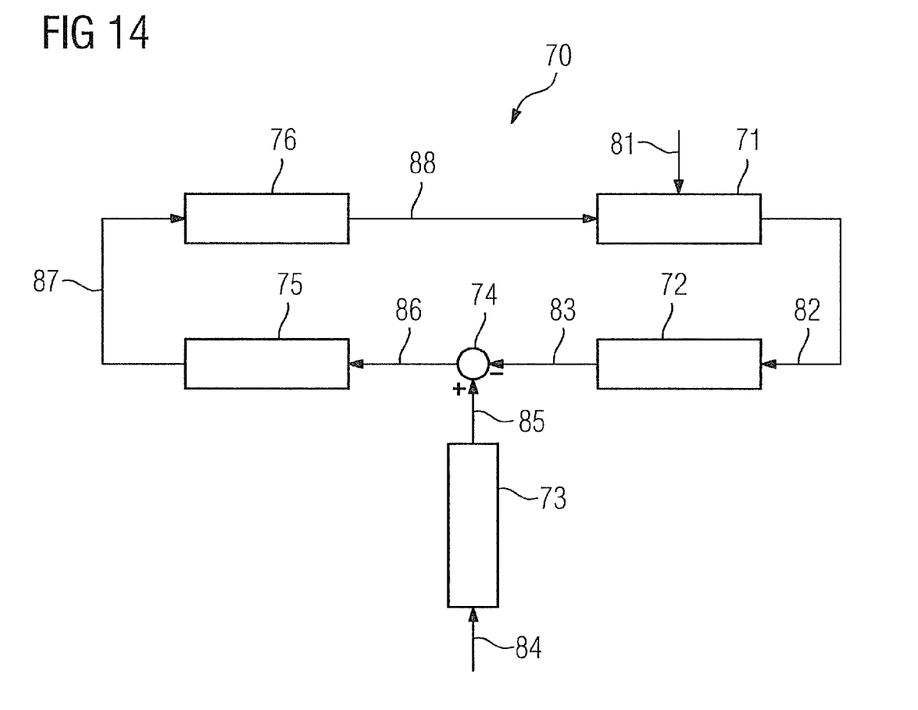
FIG. 14 shows an example of a method for controlling the movement of an X-ray apparatus.

Finally, FIG. 14 schematically illustrates an exemplary embodiment of a method 70 for controlling the movement of an X-ray apparatus. Movement control should also be understood as meaning travel involving a closed chain of effects, i.e. strictly speaking closed-loop movement control. The system to be influenced, the controlled system, is the C-arm 71, the influencing quantity 81 is an external force applied thereto, defined by a point of application, a direction of force and an absolute value of the force. As a result of the external force applied and the flexible C-arm 71, the C-arm 71 will deform not only at the point at which the external force is applied. A measuring element 72, implemented as a strain gage sensor, translates the physical measured variable 'material extension' 82, measured at a location which is generally different from the point of application of the external force, into an electrical measurement signal 83. Using a structural model 73 or a dynamic model of the C-arm 71, an expected value 85 for the electrical measured value of the deformation of the C-arm 71 at the measuring position of the sensor is calculated. The structural model 73 takes into account the mechanical structure of the C-arm 71, material properties of the components of the C-arm 71 and the reference variables 84, such as the current position of the C-arm 71, the current movement of the C-arm 71 and the current acceleration of the C-arm 71. Likewise incorporated in the structural model 73 are the mechanical structure, material properties and the dynamics of the components connected to the C-arm. A difference element 74 takes the difference 86 between the measured value 83 for the deformation of the C-arm 71 at the measuring position and the expected value 85 for the measured value of the deformation of the C-arm 71 at the measuring position. The difference 86 is a measure of the extent to which the external force deforms the C-arm in 71 in addition to the deformation of the C-arm 71 due to gravity and inertial forces. A controller 75, which is preferably implemented as a control algorithm in an electronic computer, calculates from the difference 86 a controlled variable which is preferably fed as an electrical control signal 87 to a final control element 76 comprising an actuator, e.g. a motor. The final control element 76 acts on the C-arm 71 as a function of the control signal 87 with a force 88 or an angular momentum, thereby enabling the position of the C-arm 71 to change. The control algorithm is designed such that a change in the position of the C-arm 71 counteracts an absolute value increase in the difference 86. The process is repeated continuously or in quick succession until an abort criterion, which can be in particular the actuation of an off-switch, is fulfilled.

The invention claimed is:

1. An X-ray apparatus, comprising:
    an X-ray source;
    an X-ray detector;
    a C-arm on which the X-ray source and the X-ray detector are mounted opposite one another;
    a patient table;
    an actuator that positions the C-arm relative to the patient table;
    a sensor that detects a deformation of the C-arm at a first position of the C-arm and converts the deformation into an output signal, the deformation being caused by a force exerted by an operator and applied directly or indirectly at a second position of the C-arm; and
    a control device that controls the actuator based on the output signal of the sensor so that the C-arm is controlled by the second position comprising a plurality of points of the C-arm.

2. The X-ray apparatus as claimed in claim 1, wherein the sensor comprises a strain gage.

3. The X-ray apparatus as claimed in claim 2, wherein the strain gage comprises a single-axis strain gage or a multi-axis strain gage.

4. The X-ray apparatus as claimed in claim 1, wherein the control device controls the actuator to change a position of the C-arm based on the output signal and a direction of change in position of the C-arm comprises a direction of the force exerted by the operator.

5. The X-ray apparatus as claimed in claim 4, wherein a rate of change in position of the C-arm comprises a positive correlation with the deformation of the C-arm.

6. The X-ray apparatus as claimed in claim 1, wherein the sensor is placed on the C-arm such that a change in the output signal of the sensor is greater than all other placements on the C-arm.

7. The X-ray apparatus as claimed in claim 1, wherein the deformation of the C-arm is detected by two sensors and a difference between output signals of the two sensors is fed to the control device.

8. The X-ray apparatus as claimed in claim 7, wherein the two sensors are disposed in opposite branches of a bridge circuit and an output voltage of the bridge circuit is fed to the control device.

9. The X-ray apparatus as claimed in claim 1, wherein the control device controls the actuator based on the output signal of the sensor and an expected value for the output signal of the sensor.

10. The X-ray apparatus as claimed in claim 9, wherein the expected value for the output signal of the sensor is calculable by:
    a model of mechanical structure of the C-arm and/or of the X-ray source and/or of the X-ray detector, and/or
    material properties of components of the C-arm and/or of the X-ray source and/or of the X-ray detector, and/or
    a position of the C-arm and/or of the X-ray source and/or of the X-ray detector, and/or
    a movement of the C-arm and/or of the X-ray source and/or of the X-ray detector, and/or
    an acceleration of the C-arm and/or of the X-ray source and/or of the X-ray detector.

11. A method for controlling a movement of an X-ray apparatus having a C-arm on which an X-ray source and an X-ray detector are mounted opposite one another, comprising:
    positioning the C-arm relative to a patient table by an actuator;
    detecting a deformation of the C-arm at a first position of the C-arm by a sensor;
    converting the deformation into an output signal by the sensor, the deformation being caused by a force exerted by an operator and applied directly or indirectly at a second position on the C-arm; and
    controlling the actuator by a control device based on the output signal of the sensor so that the C-arm is controlled by the second position comprising a plurality of points of the C-arm.

12. The method as claimed in claim 11, further comprising:
    detecting a measured value for the deformation of the C-arm by a measuring element comprising the sensor;
    calculating an expected value for the measured value of the deformation of the C-arm by the control device using:
        a structural model or a dynamic model of a mechanical structure of the C-arm and/or of the X-ray source and/or of the X-ray detector, and/or
        material properties of components of the C-arm and/or of the X-ray source and/or of the X-ray detector, and/or
        a current position of the C-arm and/or of the X-ray source and/or of the X-ray detector, and/or
        a current movement of the C-arm and/or of the X-ray source and/or of the X-ray detector, and/or
        a current acceleration of the C-arm and/or of the X-ray source and/or of the X-ray detector;
    calculating a control signal by the control device based on a difference between the measured value and the expected value for the measured value of the deformation of the C-arm for counteracting an absolute value increase in the difference;
    feeding the control signal to the actuator; and
    repeating the above steps until an abort criterion is fulfilled.

* * * * *